(12) United States Patent
Dai et al.

(10) Patent No.: US 11,541,376 B2
(45) Date of Patent: Jan. 3, 2023

(54) SUPPORTED CATALYST, ITS ACTIVATED FORM, AND THEIR PREPARATION AND USE

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Wei Dai, Beijing (CN); Haibin Jiang, Beijing (CN); Shuliang Lu, Beijing (CN); Xiaohong Zhang, Beijing (CN); Guoqing Wang, Beijing (CN); Jinliang Qiao, Beijing (CN); Hui Peng, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

( * ) Notice: Subject to any disclaimer, the term of this patent is extended or adjusted under 35 U.S.C. 154(b) by 458 days.

(21) Appl. No.: 15/899,988

(22) Filed: Feb. 20, 2018

(65) Prior Publication Data
US 2018/0169632 A1 Jun. 21, 2018

Related U.S. Application Data

(62) Division of application No. 14/419,736, filed as application No. PCT/CN2013/080898 on Aug. 6, 2013, now abandoned.

(30) Foreign Application Priority Data

Aug. 6, 2012 (CN) .......................... 201210277334.4

(51) Int. Cl.
| | | |
|---|---|---|
| C07C 5/02 | (2006.01) |
| B01J 25/02 | (2006.01) |
| B01J 25/00 | (2006.01) |
| C07B 35/02 | (2006.01) |
| C07B 35/06 | (2006.01) |
| C07B 35/04 | (2006.01) |
| B01J 31/28 | (2006.01) |
| B01J 31/34 | (2006.01) |
| B01J 37/00 | (2006.01) |
| C07C 1/04 | (2006.01) |
| C07C 1/06 | (2006.01) |
| C07C 29/141 | (2006.01) |

(52) U.S. Cl.
CPC ............... B01J 25/02 (2013.01); B01J 25/00 (2013.01); B01J 31/28 (2013.01); B01J 31/34 (2013.01); B01J 37/0009 (2013.01); C07B 35/02 (2013.01); C07B 35/04 (2013.01); C07B 35/06 (2013.01); C07C 1/0435 (2013.01); C07C 1/066 (2013.01); C07C 29/141 (2013.01); B01J 2231/643 (2013.01); C07C 2525/00 (2013.01); C07C 2525/02 (2013.01)

(58) Field of Classification Search
None
See application file for complete search history.

(56) References Cited

U.S. PATENT DOCUMENTS

| | | | |
|---|---|---|---|
| 3,409,474 A | 11/1968 | Jung et al. | |
| 4,826,799 A | 5/1989 | Cheng et al. | |
| 4,895,994 A * | 1/1990 | Cheng ..................... | B01J 25/00 208/217 |
| 4,987,194 A * | 1/1991 | Maeda ................ | C08F 297/046 428/462 |
| 5,536,697 A | 7/1996 | Schuetz et al. | |
| 8,735,317 B2 | 5/2014 | Mordkovich et al. | |

FOREIGN PATENT DOCUMENTS

| | | |
|---|---|---|
| CN | 1520454 A | 8/2004 |
| CN | 1557918 A | 12/2004 |
| CN | 102492940 | 6/2012 |
| CN | 102492940 A | 6/2012 |
| JP | S58112087 A | 7/1983 |
| JP | S 58112087 A | 7/1983 |
| RU | 2405625 C1 | 12/2010 |
| WO | WO 02083818 | 10/2002 |
| WO | WO02083818 A2 | 10/2002 |
| WO | WO 2010/142350 A1 | 12/2010 |

OTHER PUBLICATIONS

International Search Report issued in International Application No. PCT/CN2013/080898, dated Nov. 14, 2013 (6 pages).

* cited by examiner

Primary Examiner — Yun Qian
(74) Attorney, Agent, or Firm — Finnegan, Henderson, Farabow, Garrett & Dunner LLP (57) ABSTRACT

A supported catalyst and preparation method thereof, the catalyst comprising an organic polymer material carrier and Raney alloy particles supported on the organic polymer material carrier, wherein substantially all of the Raney alloy particles are partially embedded in the organic polymer material carrier. The catalyst can be used in hydrogenation, dehydrogenation, amination, dehalogenation or desulfuration reactions.

6 Claims, 1 Drawing Sheet

SUPPORTED CATALYST, ITS ACTIVATED FORM, AND THEIR PREPARATION AND USE

CROSS REFERENCE OF RELATED APPLICATIONS

The present application is a divisional application of U.S. patent application Ser. No. 14/419,736, filed on Feb. 5, 2015, which is a § 371 national stage application of PCT application No. PCT/CN2013/080898, filed on Aug. 6, 2013, which claims the benefit of the Chinese Patent Application No. 201210277334.4, filed on Aug. 6, 2012, the entire content of which is incorporated herein by reference in their entirety and for all purposes.

FIELD OF THE INVENTION

The present invention relates to a supported catalyst, its activated form, and their preparation and use; more particularly; to the improvement of porous catalysts prepared by Raney method.

BACKGROUND ART in the field of catalysis, "Raney method" refers to a method for preparing active metal catalysts, which method comprises: i) preparing at first a bi- or more-component alloy containing an active metal, and ii) then leaching out at least one metal component, leaving a metal having a porous structure and having a relatively high catalytically activity. Step ii) is also referred to as "activation", For example, M. Raney invented firstly Raney nickel catalyst (Industrial and Engineering Chemistry, 1940, Vol. 32, 1199), which is prepared by preparing at first a nickel-aluminum alloy, then dissolving the aluminum in the alloy with a strong caustic solution, leaving metallic nickel having a porous structure and having a very high catalytically activity.

Raney catalysts include Raney nickel catalysts, Raney cobalt catalysts, Raney copper catalysts and the like, with the Raney nickel catalysts are the most common. Raney nickel catalysts are generally present in powder form and inflammable, so that their handle is not convenient. Hence, Raney nickel catalysts are mostly used in small-scale catalytic hydrogenation reactions in fine chemical industry field, but cannot be used in conventional fixed bed reactions.

In order to expand the application field of the Raney nickel catalysts, shaping the catalysts via a certain process, particularly forming the catalysts into fixed bed catalysts, is a research direction to which more attentions have been paid recently.

Patent application CN1557918 discloses a shaped Raney nickel catalyst and the preparation thereof, which catalyst is prepared with a powdery alloy consisting of Al and one or more of Ni, Co, Cu and Fe as main material, an inorganic substance such as pseudoboehmite or the like as a binder, and a natural or synthetic organic substance such as *Sesbania cannabina* powder, carboxymethyl cellulose or the like as a pore template agent, through direct kneading, shaping, calcining, and activating with caustic solution. The resultant catalyst has a certain shape and strength, and may be used as a fixed bed catalyst.

U.S. Pat. No. 5,536,694 discloses a shaped, activated Raney metal fixed bed catalyst, which is obtained by shaping a mixture of at least one catalytic alloy powder, a pure Raney-method metal powder as a binder, shaping aids and pore-generating agent, followed by calcining and activating with an alkali solution.

U.S. Pat. No. 4,826,799 discloses a process for preparing a shaped Raney catalyst, comprising sufficiently and uniformly mixing a Raney alloy with a polymer, a mineral oil and the like at a certain temperature, then shaping the mixture with a process such as extrusion, with the polymer being burned off after the shaping or remained, and finally dissolving the metallic aluminum with a strong base to obtain an activated catalyst. A shaped catalyst can be readily obtained by said process. However, if the polymer is remained, then because the Raney alloy is wrapped or covered by the polymer during the shaping, the catalytically active sites will be less and the catalyst will have a very low or even no catalytical activity; if the polymer is burned off through a high temperature calcination, then a great deal of alloy particles may be sintered so that the activity of the catalyst will decrease.

Therefore, there is still a need to a Raney catalyst, which has a high activity, a good selectivity, and ease of metal recovery, and can be used in a fixed bed or a fluidized bed.

SUMMARY OF THE INVENTION

An objective of the present invention is to provide a supported catalyst comprising: an organic polymer material support, and Raney alloy particles supported on the organic polymer material support (particularly in the surface layer), wherein substantially all of the Raney alloy particles are partially embedded into the organic polymer material support. The catalyst may be prepared by a simple method, has less impurities, a high active metal loading amount, and a high active metal utilization ratio, and when being used in a fixed bed reaction after being activated, said catalyst have both a very high activity and a very good selectivity.

Another objective of the present invention is to provide a process for preparing the supported catalyst of the present invention.

Still another objective of the present invention is to provide an activated, supported catalyst, which comprises an organic polymer material support and activated Raney alloy particles supported on the organic polymer material support (particularly in the surface layer), wherein substantially all of the activated Raney alloy particles are partially embedded into the organic polymer material support. The activated, supported catalyst may be obtained by treating the supported catalyst of the present invention with a caustic aqueous solution.

Still another objective of the present invention is to provide the use of the activated, supported catalyst of the present invention in hydrogenation, dehydrogenation, amination, dehalogenation or desulfuration.

DETAILED DESCRIPTION OF PREFERRED EMBODIMENTS

Figure 1:
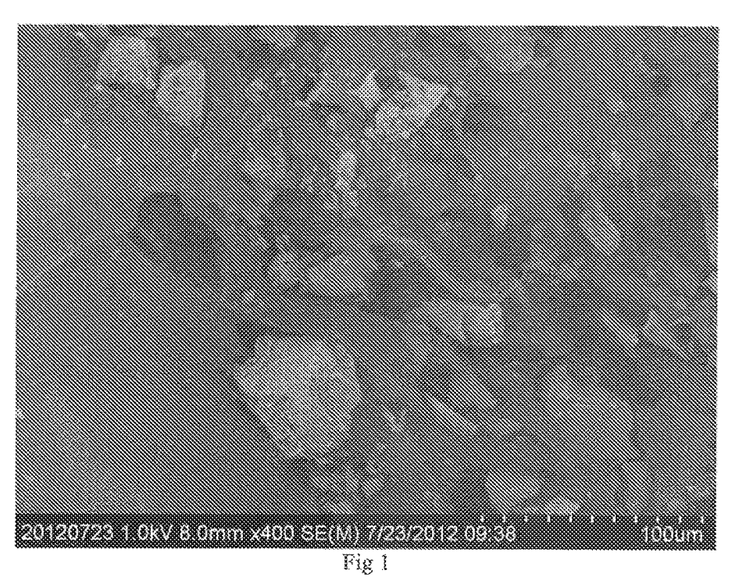
FIG. 1 is a topical scanning electron micrograph of the catalyst particles prior to activation prepared in Example 2.
Figure 2:
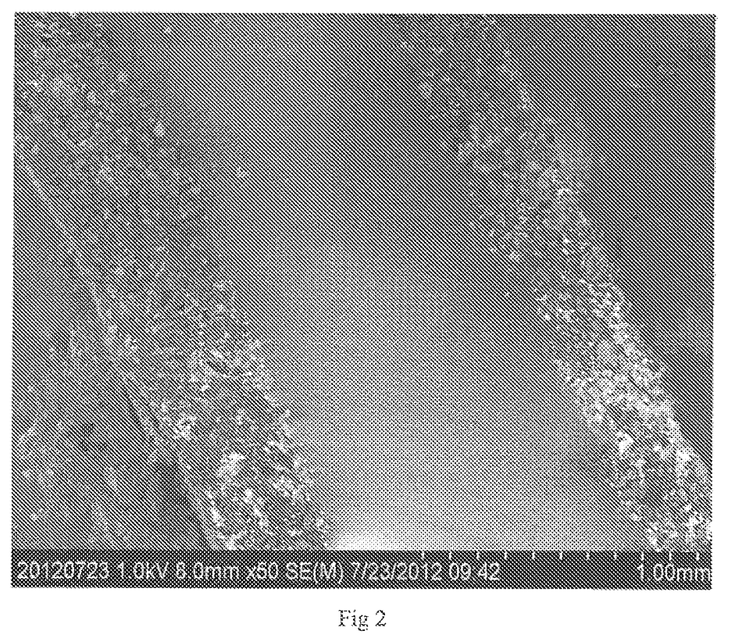
FIG. 2 is a scanning electron micrograph of a cross section of the supported catalyst sheet prepared in Example 4.

In an aspect, the present invention provides a supported catalyst comprising: an organic polymer material support and Raney alloy particles supported on the organic polymer support (particularly in the surface layer), wherein substantially all of the Raney alloy particles are partially embedded into the organic polymer material support.

As used herein, the expression "substantially all of the Raney alloy particles are partially embedded into the organic polymer material support" is intended to mean that most (for example, greater than 70 wt %, or greater than 80 wt %, or greater than 90 wt %, or greater than 95 wt %, or greater than 98 wt %, based on the total Raney alloy particles) of the Raney alloy particle comprised in the supported catalysts are partially embedded into the support, but it is allowed that there exist a minor amount (for example, less than 30 wt %, or less than 20 wt %, or less than 10 wt %, or less than 5 wt %, or less than 2 wt %, based on the total Raney alloy particles) of, for example, Raney alloy particles completely surrounded by the support material or Raney alloy particles surrounded and fixed by the Raney alloy particles partially embedded into the organic polymer material support, although such particles are less desirable.

In an embodiment, the Raney alloy comprises at least one Raney metal and at least one leachable element. As used herein, the term "Raney metal" refers to a catalytically active metal which is insoluble in the activation through the Raney method. Examples of the Raney metal include, but are not limited to, nickel, cobalt, copper, and iron. As used herein, the term "leachable element" refers to an element which is soluble in the activation through the Raney method. Examples of the leachable element include, but are not limited to, aluminum, zinc and silicon.

In a preferred embodiment, the Raney alloy is chosen from nickel-aluminum alloys, cobalt-aluminum alloys and copper-aluminum alloys.

In an embodiment, the weight ratio of the Raney metal to the leachable element in the Raney alloy ranges from 1:99 to 10:1, preferably from 1:10 to 4:1, more preferably from 1:3 to 2:1, and most preferably is 1:1.

In an embodiment, in order to enhance the activity or selectivity of the catalyst, at least promoter may be incorporated into the Raney alloy, forming a multiple-component Raney alloy. The at least one promoter may be chosen from Mo, Cr, Ti and Ru. The amount of the promoter may be from 0.01 wt % to 5 wt. % of the total weight of the Raney alloy.

The particle size of the Raney alloy particles may be selected from a wide range. For example, the average particle diameter may vary from 0.1 to 1000 microns, preferably from 1 to 500 microns, and more preferably from 10 to 100 microns.

According to the present invention, the partial embedment of substantially all of the Raney alloy particles into the organic polymer material support is accomplished by mould pressing the support surrounded by the Raney alloy particles at the mould processing temperature of the support material (fear a thermoplastic organic polymer material) or under conditions of uncure (for a thermoset organic polymer material).

As used herein, the term "the mould processing temperature of thermoplastic organic polymer material" refers to a temperature in a range of from a temperature which is higher than the softening temperature of the thermoplastic organic polymer material to the degradation temperature of the thermoplastic organic polymer material or higher. In a preferred embodiment, "the mould processing temperature of thermoplastic organic polymer material" refers to a temperature in a range of from a temperature which is 1, 3, 5 or 10° C. higher than the softening temperature of the thermoplastic organic polymer material to the degradation temperature of the thermoplastic organic polymer material.

As used herein, the expression "under conditions of uncure for thermoset organic polymer material" means that the thermoset organic polymer material has been partially cured so that it has substantially determinate shape and size, but the curing of the thermoset organic polymer material allows it to be further processed to press the Raney alloy particles thereinto.

Without limited by any specific theory, it is believed that during the mould pressing, under the action of pressure or both heat and pressure, some Raney alloy particles will be pressed into the soft/softened support and, at the same time, the soft/softened support material will overflow around the particles. The overflowed support material functions not only to fix the particles but also to provide new support surface to allow other particles to be pressed thereinto. This course occurs repeatedly so that a great deal of the Raney alloy particles are pressed into the support material. Furthermore, due to the pressing-overflowing supporting mechanism, it is expected that there are little or even no Raney alloy particles that are completely covered by material. As such, most (even if not all) of the Raney alloy particles in the supported catalyst according to the invention are accessible to the caustic aqueous solution in the sequent activation, to be converted into activated Raney catalyst particles. The present invention makes efficiently use of the surface region of the support so that the resultant supported catalyst can have a very high content of the Raney alloy and thereby the active metal. Furthermore, in the supported catalyst according to the invention, the Raney alloy particles are tightly fixed by surround support so that the catalyst has a good structural stability.

Furthermore, the mould pressing process results in that in the supported catalyst of the invention, the Raney alloy particles are distributed unevenly, with the concentration of the Raney alloy particles in the surface portion of the support material being greater than the concentration of the Raney alloy particles in the core portion of the support material. Preferably, there are little or no Raney alloy particles in the core portion of the support material. An advantage of such an uneven distribution of the Raney alloy particles in the support material is that, because there are less, little, or no Raney alloy particles in the core portion of the support material, the core portion of the support material remains its integrity and strength so that the whole supported catalyst particle has a good strength.

According to the present invention, there is not a specific limitation to the organic polymer material useful as the support, provided that it is inert and can remain sufficient rigidness under the conditions employed in the processes using the activated Raney catalysts of the invention. The organic polymer material is preferably a thermoset or thermoplastic plastic, or a modified product thereof. Examples of useful plastics include, hut are not limited to: polyolefins, such as polyethylene, polypropylene, poly-4-methyl-1-pentene; polyamides, such as Nylon-6, Nylon-12, Nylon-6/6, Nylon-6/10, Nylon-11; polycarbonate; polyformaldehydes; polyesters, such as linear polyesters formed from saturated dicarboxylic acids and diols through polycondensation reaction; aromatic ring macromolecules, i.e., polymers with molecules consisting only of aromatic rings and linking groups, such as polyphenyls, polyphenylene oxides, polyphenylene sulfides, polyarylsulphones, polyaryl ketones, polyaryl esters, aromatic polyamides; heterocycle macromolecules, i.e., polymer materials having heterocycle in addition to aromatic ring in their molecular backbone, such as polybenzoimidazole; fluorine-containing polymers; acrylic resins; carbamates; epoxy resins; phenolic resins; urea-formaldehyde resins; melamine-formaldehyde resins; polynitrile resins, such as poly(meth)acrylonitrile, (meth)acrylonitrile-styrene copolymers, acrylonitrile-styrene-butadiene copolymers; and mixtures and blends thereof. Preferably, the organic polymer material is chosen from polyolefins, polyamides, polystyrenes, epoxy resin, phenolic resins, and mixtures and blends thereof. More preferably, the organic polymer material is chosen from polypropylenes, Nylon-6, Nylon-66, polystyrenes, phenolic resins, epoxy resin, and mixtures and blends thereof.

As used herein, the term "modified product of plastic" refers to a modified product obtained by modifying a plastic with any plastic modifying methods known in the art. The plastic modifying methods include, but are not limited to: grafting modification using a polar or apolar monomer or a polymer thereof; modification accomplished by melt blending with an inorganic or organic reinforcing material; toughening material, rigidity-enhancing material, heat resistance-enhancing material; and the like. Some plastic blends may also be considered as modified products of plastic. Examples of useful modified product of plastic include: polypropylene blending-modified polyethylene; maleic anhydride-grafted polypropylene, elastomer-toughened polypropylene, calcium carbonate-modified. Nylon, glassfiber-modified Nylon, high impact polystyrenes, elastomer-modified epoxy resin, and the like.

In an embodiment, the supported catalyst comprises 2 to 95 wt. % of the Raney alloy, and 5 to 98 wt. % of the organic polymer material support, based on the total weight of the supported catalyst. Preferably, the supported catalyst comprises 10 to 90 wt. % of the Raney alloy, and 10 to 90 wt. % of the organic polymer material support, based on the total weight of the supported catalyst.

There is not a specific limitation to the shape of the supported catalyst of the invention, as long as it is suitable to the fixed bed or fluidized bed processes, especially fixed bed processes. Conveniently, the supported catalyst may be in the form of sphere, semi-sphere, ring, semi-ring, trilobal extrudate, cylinder, semi-cylinder, hollow cylinder, prism, cube, cuboid, tablet, pellet, irregular particles such as those obtained by breaking a sheet, and the like.

The particle size of the supported catalyst of the invention may vary widely, depending on the preparation method and intended use of the catalyst. The average equivalent diameter of the particles of the supported catalyst typically ranges from 0.3 mm to 20 mm, preferably from 0.5 mm to 10 mm, and more preferably from 1 mm to 8 mm.

In another aspect, the present invention provides a process for preparing the supported catalyst described above, which process comprises: mould pressing an organic polymer material support surrounded by the Raney alloy particles at the mould processing temperature of the organic polymer material (for a thermoplastic organic polymer material) or under conditions of uncure (for a thermoset organic polymer material).

For different organic polymer material supports, the specific preparation processes are slightly different.

In some embodiments where a thermoplastic organic polymer material is used as the support, the supported catalyst may be prepared by the following process (i) or (ii):

process (i) comprising the steps of:
(1) providing thermoplastic organic polymer material particles having desired size and shape;

(2) placing the organic polymer material particles in Raney alloy particles so as to make the organic polymer material particles completely surrounded by the Raney alloy particles;

(3) pressing the mixture of the Raney alloy particles and the thermoplastic organic polymer material particles at the mould processing temperature of the thermoplastic organic polymer material, so as to push a certain amount of the Raney alloy particles at least partially into the thermoplastic organic polymer material support particles;

(4) cooling, then sieving, to obtain particulate supported catalyst.

The particle size and shape of the obtained particulate supported catalyst are as described above.

The thermoplastic organic polymer material particles may be prepared by any methods known in the art. In some embodiments, the thermoplastic organic polymer material particles may be prepared from the powder of the organic polymer material through a process such as extruding and pelleting process and molding process. In other embodiments, it is also possible to directly use commercially available, shaped thermoplastic organic polymer material particles.

Process (ii) comprising the steps of:
(1) providing a thermoplastic organic polymer material sheet having a desired thickness;
(2) uniformly spreading Raney alloy particles on one or both of the upper and lower surfaces of the sheet, preferably the both;
(3) pressing the sheet having the Raney alloy particles spread thereon at the mould processing temperature of the thermoplastic organic polymer material, so as to push a certain amount of the Raney alloy particles at least partially into the sheet, to obtain a support sheet carrying the Raney alloy particles in its surface layer;
(4) optionally after cooling, forming the support sheet carrying the Raney alloy particles on its surface into particles having desired shape and size, to obtain particulate supported catalyst.

For the above processes (i) and (ii), the Raney alloy particles are as described above.

In step (3) of the above processes (i) and (ii), the applied pressure is generally in a range of from 0.5 MPa to 20 MPa, and preferably from 2 to 10 MPa. Those skilled in the art will understand, if a higher temperature is used, then a lower pressure may be employed, and if a lower temperature is used, then a higher pressure may be employed.

In step (3) of the above processes (i) and (ii), the duration of applying pressure is dependent on the temperature and pressure employed as well as the desired loading level of the Raney alloy particles, and may be readily determined by those skilled in the art.

In an embodiment, the pressure is continuously applied in the course of the cooling in step (4).

In step (4) of the process (ii), the support sheet carrying the Fancy alloy particles on its surface may be formed into particles having desired shape and size by any method known in the art, such as cutting, tailoring, punching, or breaking.

Optionally in the process (i) or the process (ii), the thermoplastic support may comprise auxiliaries commonly used in plastic processing, for example, antioxidants, heat stabilizers, photostabilizers, ozone resistants, processing aids, plasticizers, softening agents, anti-blocking agents, foaming agents, dyes, pigments, waxes, extenders, flame retardants, and coupling agents. The amounts of the auxiliaries used may be those conventionally employed, or may be adjusted according to actual demand.

In some embodiments where a thermoset organic polymer material is utilized as the support, the supported catalyst may be prepared the following process (iii), (iv) or (v):

process (iii) comprising the steps of:

(1) formulating a curable composition, which is curable to a thermoset organic polymer material, and which may be a liquid system or a powdery solid system;

(2) to a mould having a desired particle size and cavity shape suitable for fixed bed catalysts or fluidized bed catalysts, adding first Raney alloy particles, then the curable composition formulated in step (1), and then the Raney alloy particles, and then subjecting the thermoset organic polymer material to partially curing treatment, to provide a partially cured particulate support surrounded by the Raney alloy particles;

(3) then, pressing the partially cured particulate support surrounded by the Raney alloy particles to push a certain amount of the Raney alloy particles at least partially into the particulate support and, at the same time or thereafter, completely curing the thermoset organic polymer material; and (4) sieving, to obtain particulate supported catalyst, process (iv) comprising the steps of:

(1) formulating a curable composition, which is curable to a thermoset organic polymer material, and which may be a liquid system or a powdery solid system;

(2) partially curing the curable composition in a suitable mould to provide a partially cured organic polymer material sheet, wherein the curing degree is such that the partially cured organic polymer material allows Raney alloy particles to be pressed thereinto in a sequent step;

(3) uniformly spreading Raney alloy particles on one or both of the upper and lower surfaces of the sheet;

(4) pressing the sheet having the Raney alloy particles spread thereon so as to push a certain amount of the Raney alloy particles at least partially into the sheet and, at the same time or thereafter, completely curing the thermoset organic polymer material; and (5) forming the sheet from step (4) into particles having desired shape and size, to obtain particulate supported catalyst, process (v) comprising the steps of:

(1) preparing partially cured thermoset organic polymer material particles having desired shape and size from a curable composition which is curable to the thermoset organic polymer material, with the curing degree of the partially cured thermoset organic polymer material particles being such that it allows Raney alloy particles to be pressed thereinto in a sequent step;

(2) placing the partially cured thermoset organic polymer material particles in the Raney alloy particles so as to make them completely surrounded by the Raney alloy particles;

(3) pressing the mixture of the Raney alloy particles and the partially cured thermoset organic polymer material particles to push a certain amount of the Raney alloy particles at least partially into the organic polymer material support particles and, at the same time or thereafter, completely curing the partially cured thermoset organic polymer material; and (4) sieving, to obtain the particulate supported catalyst.

In the above process (iii), (iv) or (v), the curable composition per se is known by those skilled in the art. The curable composition may optionally comprise one or more additives chosen from: curing accelerators, dyes, pigments, colorants, antioxidants, stabilizers, plasticizers, lubricants, flow modifiers or promoters, flame retardants, antifogging agents, anti-blocking agents, adhesion promoters, conductive additives, multi-valent metal ions, impact modifiers, releasing agents, and nucleating agents. If present, such additives may be included in a conventional amount, or their amounts may be adjusted according to the actual demand.

For the above processes (iii)-(v), the Raney alloy particles are as described above.

In the pressing step of the above processes (iii)-(v), the applied pressure is generally in a range of from 0.5 MPa to 20 MPa, and preferably from 2 to 10 MPa. Those skilled in the art will appreciate that, if the partially cured organic polymer material is low in curing degree so that it has a large deformability, then a low pressure may be employed, while if the partially cured organic polymer material is high in curing degree so that it has a small deformability, then a high pressure may be employed.

In the pressing step of the above processes (iii) to (v), the duration of applying pressure is depended on the curing degree of the partially cured organic polymer material, the temperature and pressure employed, and the desired loading level of the Raney alloy particles, and may be readily determined by those skilled in the art. In an embodiment, the applying of the pressure is lasted till the completion of the curing of the organic polymer material.

In step (5) of the process (iv), the support sheet carrying the Raney alloy particles on its surface may be formed into particles having desired shape and size by any method known in the art, such as cutting, tailoring, punching, or breaking.

In a further aspect, the present invention provides an activated, supported catalyst, which comprises an organic polymer material support and activated Raney alloy particles supported on the organic polymer material support (particularly in its surface layer), wherein substantially all of the activated Raney alloy particles are partially embedded into the organic polymer material support.

As used herein, the expression "substantially all of the activated Raney alloy particles are partially embedded into the organic polymer material support" is intended to mean that most (for example, greater than 70 wt %, or greater than 80 wt %, or greater than 90 wt %, or greater than 95 wt %, or greater than 98 wt %) of the activated Raney alloy particle comprised in the activated, supported catalysts are partially embedded into the support, but it is allowed that there exist a minor amount (for example, less than 30 wt %, or less than 20 wt %, or less than 10 wt %, or less than 5 wt %, or less than 2 wt %) of, for example, activated Raney alloy particles surrounded and fixed by the activated Raney alloy particles partially embedded into the organic polymer material support, although such particles are less desirable.

The activated, supported catalyst of the invention may be prepared by activating the supported catalyst of the invention.

Methods for activating the supported catalyst and conditions employed therein are known per se. For example, the supported catalyst may be activated by treating it with a caustic aqueous solution having a concentration of from 0.5 to 50 wt. %, preferably from 1 to 40 wt. %, and more preferably from 5 to 30 wt. % at a temperature of 25° C. to 95° C. for about 5 minutes to 72 hours, to leach out at least a portion of the leachable element, for example, at least one of aluminum, zinc, and silicon, present in the Raney alloy. In an embodiment, the caustic aqueous solution is sodium hydroxide aqueous solution or potassium hydroxide aqueous solution.

Since there are substantially no (if any, in an amount of less than 30 wt %, or less than 20 wt %, or less than 10 wt %, or less than 5 wt %, or less than 2 wt %, based on the total Raney alloy particles) Raney alloy particles, which are completely surrounded by the organic polymer material as support, thereby not accessible to the caustic aqueous solution, in the supported catalyst of the invention, the activated, supported catalyst of the invention comprises substantially no unactivated Raney alloy particles.

By controlling the loading amount of Raney alloy particles in the preparation of the catalyst and/or controlling the activation degree of the catalyst, the loading amount of the Raney metal in the activated catalyst may be readily controlled. In an embodiment, the loading amount of the Raney metal in the activated, supported catalyst of the invention ranges from 1 to 90 wt. %, preferably from 10 to 80 wt. %, and more preferably from 40 to 80 wt. %, based on the total weight of the activated, supported catalyst.

The activated, supported catalyst of the invention has a good strength and can be used for fixed bed or fluidized bed catalytic reactions.

The activated, supported catalyst of the invention may be used for hydrogenation, dehydrogenation, amination, dehalogenation, desulfuration, and the like, preferably hydrogenation, such as olefin hydrogenation, alkyne hydrogenation, arene hydrogenation, carbonyl hydrogenation, nitro hydrogenation, nitrile hydrogenation, and more preferably aldehyde hydrogenation to alcohol, hydrogenation of CO, hydrogenation of benzene, or hydrogenation of nitrobenzene to aniline.

Therefore, in a further aspect, the present invention provides use of the activated, supported catalyst of the invention in hydrogenation, dehydrogenation, amination, dehalogenation, or desulfuration.

In some embodiments, the present invention relates to a process of converting an organic compound, which process comprises contacting the organic compound feedstock with the activated, supported catalyst of the invention under suitable conversion conditions, and recovering converted organic compound.

In a particular embodiment, the present invention relates to a process for hydrogenating an organic compound, which process comprises contacting the organic compound feedstock with the activated, supported catalyst of the invention in the presence of hydrogen under suitable hydrogenation conditions, and recovering hydrogenated organic compound.

In an embodiment, the conversion process or the hydrogenation process is a fixed bed or fluidized bed process.

The process conditions of the conversion process are well known by those skilled in the art.

In the preparation of conventional metal/inorganic oxide-support catalyst prepared through impregnation process, there need multiple times of impregnating and calcining, and its metal loading amount can hardly exceed 40 wt. %, based on the total weight of the catalyst. Furthermore, because the high-temperature calcination used in the preparation results in the sintering of many metal particles, the utilization ratio of the active metal is low so that the activity of the catalyst is low. Although a catalyst having a high metal content can be obtained through a blending process or a co-precipitating process, because many metal particles are surrounded by non-active component, the utilization ratio of the metal is very low so that the activity of the catalyst is very low. Not only the catalyst of the invention can have a high loading level of active metal, but also it has a high utilization ratio of the active metal due to that no high-temperature treatment is used in the preparation and most (even if not all) of Raney alloy particles are accessible to the caustic aqueous solution in the sequent activation process. Thus, the activated catalyst of the invention has a high activity.

Furthermore, the processes for preparing the catalyst of the invention are simple and low in cost. Furthermore, it is possible that the catalyst of the invention does not contain an inorganic auxiliary so that the catalyst has almost no acidic or basic sites on its surface and thereby can exhibit good selectivity in a catalytic reaction. Additionally, the catalyst of the invention has a high metal content in its surface layer so that it has good heat transfer performance. The catalyst of the invention also allows the easy recovery of the metal from the spent catalyst and the pollution during the recovery is light.

EXAMPLES

The following examples are given for further illustrating the invention, but do not make limitation to the invention in any way.

Example 1

The Preparation of a Raney Ni/Polypropylene Catalyst:

Powdery polypropylene (Maoming Petrochemical, F280M) was extruded with a twin screw extruder and cut into particles of Φ3 mm×3 to 5 mm. 50 Grams of the polypropylene particles were placed in 2000 g of 100 to 200 mesh powdery nickel-aluminum alloy having a Ni content of 48 wt. % and an aluminum content of 52 wt. %. The mixture of the polypropylene particles and the powdery nickel-aluminum alloy was mould pressed in a platen press at 200° C. under a pressure of 7 MPa for 10 min, then removed and cooled. The mixture was sieved to separate catalyst particles from the excessive powdery nickel-aluminum alloy to obtain 200 g supported catalyst. It was visually observed that the surface of the catalyst particles was completely covered by the nickel-aluminum alloy powder.

400 g of 20 wt % NaOH aqueous solution was formulated with deionized water and added to 40 g of the above-prepared supported catalyst particles. The resultant mixture was maintained at 85° C. for 4 hours, then the liquid was filtered off, and the solids were washed with deionized water to near neutrality, to obtain an activated catalyst. The activated catalyst was conserved in deionized water for use. The activated catalyst was found to have a nickel content of 45 wt. %, based on the weight of the activated catalyst.

Example 2

The Preparation of a Raney Ni/Polypropylene Catalyst:

Powdery polypropylene (Maoming Petrochemical, F280M) was mould pressed in a platen press at 200° C. under a pressure of 7 MPa for 10 min, to form a sheet having a thickness of approximate 2 mm.

In the platen press, two layers of 100 mesh to 200 mesh powdery nickel-aluminum alloy each having a thickness of about 2 mm were spread above and below a polypropylene sheet weighing 20 g prepared above, respectively, with the nickel-aluminum alloy having a Ni content of 48 wt. % and an aluminum content of 52 wt. %. Mould pressing was carried out at a temperature of 200° C. under a pressure of 7 MPa for 10 min, then the polypropylene sheet was removed and cooled, to afford a supported catalyst sheet weighing 120 g. It was visually observed that both the upper and lower surfaces of the polypropylene sheet were covered completely by the nickel-aluminum alloy powder.

The catalyst sheet was mechanically cut into particles having a particle size of about 3 to 5 mm.

400 g of 20 wt % NaOH aqueous solution was formulated with deionized water and added to 40 g of the above-prepared catalyst particles. The resultant mixture was maintained at 85° C. for 8 hours, then the liquid was filtered off, and the solids were washed with deionized water to near neutrality, to obtain an activated catalyst. The activated catalyst was conserved in deionized water for use. The activated catalyst was found to have a nickel content of 45 wt. %, based on the weight of the activated catalyst.

Example 3

The Preparation of a Raney Ni/Nylon-6 Catalyst

50 Grams of Nylon-6 particles (Baling Petrochemical, BL2340-H, having a particle size of (Φ2.5×3 mm) were placed in 2000 g of 100 to 200 mesh powdery nickel-aluminum alloy having a Ni content of 48 wt. % and an aluminum content of 52 wt. %. The mixture of the Nylon-6 particles and the powdery nickel-aluminum alloy was mould pressed in a platen press at 250° C. under a pressure of 7 MPa for 10 min, then removed and cooled. The mixture was sieved to separate catalyst particles from the excessive powdery nickel-aluminum alloy, to obtain 210 g supported catalyst. It was visually observed that the surface of the catalyst particles was completely covered by the nickel-aluminum alloy powder.

400 g of 20 wt % NaOH aqueous solution was formulated with deionized water and added to 40 g of the above-prepared supported catalyst particles. The resultant mixture was maintained at 85° C. for 4 hours, then the liquid was filtered off, and the solids were washed with deionized water to near neutrality, to obtain an activated catalyst. The activated catalyst was conserved in deionized water for use. The activated catalyst was found to have a nickel content of 45 wt. %, based on the weight of the activated catalyst.

Example 4

The Preparation of a Raney Ni/Nylon-6 Catalyst:

Nylon-6 (Baling Petrochemical, BL2340-H) was mould pressed in a platen press at 250° C. under a pressure of 7 MPa for 10 min, to form a sheet having a thickness of approximate 2 mm.

In the platen press, two layers of 100 mesh to 200 mesh powdery nickel-aluminum alloy each having a thickness of about 2 mm were spread above and below a Nylon-6 sheet weighing 20 g prepared above, respectively, with the nickel-aluminum alloy having a Ni content of 48 wt. % and an aluminum content of 52 wt. %. Mould pressing was carried out at a temperature of 250° C. under a pressure of 7 MPa for 10 min, then the Nylon-6 sheet was removed and cooled, to afford a supported catalyst sheet weighing 180 g. It was visually observed that both the upper and lower surfaces of the Nylon-6 sheet were covered completely by the nickel-aluminum alloy powder.

The catalyst sheet was mechanically cut into particles having a particle size of about 3 to 5 mm.

400 g of 20 wt % NaOH aqueous solution was formulated with deionized water and added to 40 g of the above-prepared catalyst particles. The resultant mixture was maintained at 85° C. for 8 hours, then the liquid was filtered off, and the solids were washed with deionized water to near neutrality, to obtain an activated catalyst. The activated catalyst was conserved in deionized water for use. The activated catalyst was found to have a nickel content of 50 wt. %, based on the weight of the activated catalyst.

Example 5

The Preparation of a Raney Ni/Mo/Nylon-6 Catalyst:

Nylon-6 (Baling Petrochemical, BL2340-H) was mould pressed in a platen press at 250° C. under a pressure of 7 MPa for 10 min, to form a sheet having a thickness of approximate 2 mm.

In the platen press, two layers of 100 mesh to 200 mesh powdery nickel-molybdenum-aluminum ternary alloy each having a thickness of about 2 mm were spread above and below a Nylon-6 sheet weighing 20 g prepared above, respectively, with the nickel-molybdenum-aluminum alloy having a Ni content of 48 wt. %, an aluminum content of 50 wt. %, and a molybdenum content of 2 wt. %. Mould pressing was carried out at a temperature of 250° C. under a pressure of 7 MPa for 10 min, then the Nylon-6 sheet was removed and cooled, to afford a supported catalyst sheet weighing 180 g. It was visually observed that both the upper and lower surfaces of the Nylon-6 sheet were covered completely by the nickel-molybdenum-aluminum alloy powder.

The catalyst sheet was mechanically cut into particles having a particle size of about 3 to 5 mm.

400 g of 20 wt % NaOH aqueous solution was formulated with deionized water and added to 40 g of the above-prepared catalyst particles. The resultant mixture was maintained at 85° C. for 8 hours, then the liquid was filtered off, and the solids were washed with deionized water to near neutrality, to obtain an activated catalyst. The activated catalyst was conserved in deionized water for use. The activated catalyst was found to have a nickel content of 45 wt. %, based on the weight of the activated catalyst.

Example 6

The Preparation of a Raney Cu/Nylon-6 Catalyst:

Nylon-6 (Baling Petrochemical, BL2340-H) was mould pressed in a platen press at 250° C. under a pressure of 7 MPa for 10 min, to form a sheet having a thickness of approximate 2 mm.

In the platen press, two layers of 100 mesh to 200 mesh powdery copper-aluminum alloy each having a thickness of about 2 mm were spread above and below a Nylon-6 sheet weighing 20 g prepared above, respectively, with the copper-aluminum alloy having a Cu content of 46 wt. % and an aluminum content of 54 wt. %. Mould pressing was carried out at a temperature of 250° C. under a pressure of 7 MPa for 10 min, then the Nylon-6 sheet was removed and cooled, to afford a supported catalyst sheet weighing 180 g. It was visually observed that both the upper and lower surfaces of the Nylon-6 sheet were covered completely by the copper-aluminum alloy powder.

The catalyst sheet was mechanically cut into particles having a particle size of about 3 to 5 mm.

400 g of 20 wt % NaOH aqueous solution was formulated with deionized water and added to 40 g of the above-prepared catalyst particles. The resultant mixture was maintained at 85° C. for 48 hours, then the liquid was filtered off, and the solids were washed with deionized water to near neutrality, to obtain an activated catalyst. The activated catalyst was conserved in deionized water for use. The activated catalyst was found to have a Cu content of 65 wt. %, based on the weight of the activated catalyst.

Example 7

The Preparation of a Raney Ni/Thermoset Epoxy Resin Catalyst:

A curable epoxy resin system was prepared by stirring uniformly 100 parts by mass of liquid epoxy resin (Baling Petrochemical, CYD-128), 85 parts by mass of methyl tetrahydrophthalic anhydride (MeTHPA) (available from Shengshida Technology and Trade Corp., Ltd., Guangdong) as a curing agent, and 1.5 parts by mass of triethanolamine (TEA) (available from Tianjin Chemical Reagent First Factory) as a curing accelerator.

50 Grams of the above-prepared curable epoxy resin system were added uniformly with a dropper into a mould having Φ5 mm cylindrical pores (total 400 pores), to which 500 g of 100 mesh to 200 mesh powdery nickel-aluminum alloy having a Ni content of 48 wt. % and an aluminum content of 52 wt. % had been added. Then the mould was filled with additional 500 g of the same powdery nickel-aluminum alloy. The mould was placed into a platen press and then mould pressed at a temperature of 120° C. under a pressure of 7 MPa for 30 minutes. Partially cured epoxy resin particles containing some powdery nickel-aluminum alloy were separated. The particles were placed in additional 1000 g of powdery nickel-aluminum alloy, then the resultant mixture was mould pressed in the platen press at a temperature of 150° C. under a pressure of 7 MPa for 90 minutes, then removed and cooled. The mixture was sieved to separate catalyst particles from the excessive powdery nickel-aluminum alloy, to obtain 180 g supported catalyst. It was visually observed that the surface of the catalyst particles was completely covered by the nickel-aluminum alloy powder.

400 g of 20 wt % NaOH aqueous solution was formulated with deionized water and added to 40 g of the above-prepared supported catalyst particles. The resultant mixture was maintained at 85° C. for 8 hours, then the liquid was filtered off, and the solids were washed with deionized water to near neutrality, to obtain an activated catalyst. The activated catalyst was conserved in deionized water for use. The activated catalyst was found to have a nickel content of 55 wt. %, based on the weight of the activated catalyst.

Example 8

The Preparation of a Raney Ni/Polypropylene Catalyst:

400 g of 10 wt % NaOH aqueous solution was formulated with deionized water and added to 40 g of the supported catalyst particles prepared in Example 1. The resultant mixture was maintained at 90° C. for 15 minutes, then the liquid was filtered off and the solids were washed with deionized water to near neutrality, to obtain an activated catalyst. The activated catalyst was conserved in deionized water for use. The activated catalyst was found to have a nickel content of 40 wt. %, based on the weight of the activated catalyst.

Comparative Example 1

Alumina Supported Metallic Nickel as a Low-Temperature Methanation Catalyst:

An alumina supported metallic nickel catalyst was prepared through impregnation process according to Example 1 of patent CN100490972C. Said catalyst comprises 40 wt. % of metallic nickel, and can be used in low-temperature methanation reaction to remove a trace amount of CO in hydrogen gas.

Comparative Example 2

Alumina Supported Metallic Nickel as an Aldehyde Hydrogenation Catalyst:

291 Grams of $Ni(NO_3)_2 \cdot 6H_2O$ were dissolved in 150 g of deionized water, and 103 g of pseudoboehmite were added thereto. To the reaction was added dropwise 5% NaOH solution with stirring until the nickel precipitation was completed. A mixture of the pseudoboehmite and nickel hydroxide was filtered out and washed to near neutrality, dried at 120° C., calcined at 500° C., and then tabletted, to afford an alumina supported nickel catalyst. After having been reduced with hydrogen gas at 450° C., said catalyst contains 45 wt. % of metallic nickel and can be used in the aldehyde hydrogenation reaction to prepare an alcohol.

Comparative Example 3

10 g of powdery polypropylene and 100 g of powdery nickel-aluminum alloy having a Ni content of 48 wt. % and an aluminum content of 52 wt. % were blended in a high-speed blender, then extruded from a twin screw extruder at an extrusion temperature of 200° C. The extrudates were cut into little cylindrical particles sizing Φ3 mm×3 mm.

400 g of 20 wt % NaOH aqueous solution was formulated with deionized water and added to 40 g of the above-prepared cylindrical particles of nickel-aluminum alloy and polypropylene. The resultant mixture was maintained at 85° C. for 8 hours, then the liquid was filtered off, and the solids were washed with deionized water to near neutrality, to obtain an activated catalyst. The activated catalyst was conserved in deionized water for use. The activated catalyst was found to have a nickel content of 45 wt. %, based on the weight of the activated catalyst.

Comparative Example 4

Fixed Bed Raney Nickel Catalyst Containing Alumina as a Binder:

Catalyst particles sizing Φ3 mm×3 mm were prepared according to the process described in Examples of patent application CN1557918A. The final catalyst has a Ni content of 50 wt. %.

Example 9

Performance Test in CO Methanation Reaction:

6 ml of catalyst were charged into a stainless steel fixed bed reactor, and then highly pure nitrogen gas was passed through the reactor at a flow rate of 300 ml/min. The reactor was heated to 120° C. and maintained at that temperature for 2 hours. Then, the highly pure nitrogen gas flow was switched to hydrogen gas at a flow rate of 300 ml/min, and the reactor was heated to 150° C. Next, a crude hydrogen feedstock containing 5500 ppm CO was introduced to start the reaction, with the reaction pressure being 0.1 MPa. The flow rate of the crude hydrogen feedstock and the reaction temperature were altered to obtain reaction results under different conditions. The composition of gases after reaction was analyzed by a gas phase chromatograph with FID as a detector, with the CO content being rounded to 1 ppm.

By using the above evaluation method, the catalysts of Examples 1 to 5, Examples 7 to 8 and Comparative Examples 1 and 3 were evaluated, and the evaluation results are given in Table 1 below. A smaller CO content at outlet (ppm) indicates a higher catalyst activity.

TABLE 1

Evaluation results of catalyst in CO methanation reaction

| No. | Composition | Loading amount of active metal wt. % | Reaction temperature (° C.) | Flow rate of crude hydrogen (ml/min) | Outlet CO (ppm) |
|---|---|---|---|---|---|
| Example 1 | Raney nickel/polypropylene | 45 | 166 | 600 | 202 |
| Example 2 | Raney nickel/polypropylene | 45 | 166 | 600 | 165 |
| Example 3 | Raney nickel/Nylon-6 | 45 | 166 | 600 | 57 |
| Example 5 | Raney nickel/Mo/Nylon-6 | 45 | 166 | 600 | <1 |
| Example 4 | Raney nickel/Nylon-6 | 50 | 166 | 800 | <1 |
| Example 7 | Raney nickel/epoxy resin | 55 | 166 | 600 | <1 |
| Example 8 | Raney nickel/polypropylene | 40 | 166 | 600 | 240 |
| Comparative Example 1 | nickel/alumina | 40 | 166 | 600 | 537 |
| Comparative Example 3 | Blended Raney nickel/polypropylene | 45 | 166 | 600 | 5500 |

It can be seen from the results in Table 1 that the CO contents at outlet of the inventive Examples are much lower than that of the comparative Examples, indicating that the catalysts of the invention have higher low-temperature methanation activities.

Example 10

Performance Test in Aldehyde Hydrogenation Reaction:

The performance of catalysts in reaction was evaluated by using fixed bed n-butanal liquid-phase hydrogenation test. 20 ml of catalyst were charged into a fixed bed reactor, and n-butanal liquid-phase hydrogenation test was carried out under conditions of a hydrogen flow rate of 50 ml/min, a reaction temperature of 90 to 150° C., a pressure of 4.0 MPa, and a liquid hourly space velocity of n-butanal of 0.3 h$^{-1}$. Reaction product was quantified by a gas phase chromatograph with FID as a detector.

TABLE 2

Activity of catalysts in aldehyde hydrogenation reaction

| | Catalyst | | | | | | |
|---|---|---|---|---|---|---|---|
| | | Loading amount of active metal | Aldehyde conversion (%), reaction temperature | | | | |
| No. | Composition | wt. % | 90° C. | 100° C. | 110° C | 130° C. | 150° C. |
| Example 1 | Raney nickel/polypropylene | 45 | 99.975 | 99.989 | 99.999 | 99.999 | — |
| Example 4 | Raney nickel/Nylon-6 | 50 | 99.983 | 99.999 | 99.999 | 99.999 | 99.999 |
| Example 6 | Raney copper/Nylon-6 | 65 | 99.901 | 99.925 | 99.955 | 99.983 | 99.985 |
| Example 7 | Raney nickel/epoxy resin | 55 | 99.957 | 99.999 | 99.991 | 99.999 | 99.999 |
| Comparative Example 2 | nickel/alumina | 45 | 90.500 | 93.50 | 95.500 | 98.900 | 99.900 |
| Comparative Example 3 | Blended Raney nickel/polypropylene | 45 | <1 | <1 | <1 | <1 | <1 |
| Comparative Example 4 | Raney nickel/alumina | 50 | 99.078 | 99.530 | 99.899 | 99.987 | 99.990 |

TABLE 3

Amount of ether byproduct generated in the aldehyde hydrogenation reaction

| | Catalyst | | | | | | |
|---|---|---|---|---|---|---|---|
| | | loading amount of active metal | Content of n-butyl ether in the effluent (wt. %), reaction temperature | | | | |
| No. | Composition | wt. % | 90° C. | 100° C. | 110° C | 130° C. | 150° C. |
| Example 1 | Raney nickel/polypropylene | 45 | 0.013 | 0.053 | 0.096 | 0.449 | to |
| Example 4 | Raney nickel/Nylon-6 | 50 | 0.000 | 0.020 | 0.015 | 0.016 | 0.035 |
| Example 6 | Raney copper/Nylon-6 | 65 | 0.000 | 0.005 | 0.010 | 0.024 | 0.030 |
| Example 7 | Raney nickel/epoxy resin | 55 | 0.014 | 0.022 | 0.081 | 0.501 | 1.373 |
| Comparative Example 2 | nickel/alumina | 45 | 0.159 | 0.292 | 0.677 | 1.706 | 2.210 |
| Comparative Example 3 | Blended Raney nickel/polypropylene | 45 | not detectable | not detectable | not detectable | not detectable | not detectable |
| Comparative Example 4 | Raney nickel/alumina | 50 | 0.243 | 0.425 | 0.647 | 1.126 | 1.520 |

The conversion results in the aldehyde hydrogenation reaction were shown in Table 2, reflecting how the catalyst activity is. A higher conversion indicates a higher catalyst activity. The results regarding the formation of n-butyl ether byproduct in the aldehyde hydrogenation reaction were shown in Table 3, reflecting how the catalyst selectivity is. A less amount of the formed ether indicates a better selectivity of the catalytic reaction.

It can be seen from the evaluation results in Table 2 and Table 3 that the present catalysts are significantly superior to the catalysts of Comparative Examples in both activity and selectivity, and this means a great application value in industrial production. Comparative Example 3 has almost no activity. Maybe the reason is that the metal component is wrapped or covered almost completely by the polymer so that the amount of the catalytically active sites is very small. Since the conversion for Comparative Example 3 is very low, the n-butyl ether byproduct is not detectable. Comparative Example 4 is a fixed bed Raney nickel catalyst containing alumina, which has an activity in the aldehyde hydrogenation slightly lower than that of the present catalyst, but results in the formation of relatively much n-butyl ether byproduct, indicating that it is markedly inferior to the present catalyst in selectivity.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. The present invention has been described above with reference to many embodiments and specific examples. Considering the above detailed description, many variations will be apparent for those skilled in the art. All of such variations will be within the scope of the whole purpose of the appended claims In this disclosure, whenever a composition, an element or a group of elements is preceded with the transitional phrase "comprising", it is understood that we also contemplate the same composition, element or group of elements with transitional phrases "consisting essentially of", "consisting of", "selected from the group of consisting of", or "is" preceding the recitation of the composition, element, or elements and vice versa.

What is claimed is:

1. A process for preparing a particulate supported catalyst, comprising the steps of:
   (1) providing thermoplastic organic polymer material particles;
   (2) placing the organic polymer material particles in Raney alloy particles so as to make the organic polymer material particles completely surrounded by the Raney alloy particles;
   (3) pressing in a platen press the mixture of the Raney alloy particles and the thermoplastic organic polymer material particles at the mould processing temperature ranging from 200° C.-250° C. and a pressure between 7 MPa and 20 MPa of the thermoplastic organic polymer material so as to push a portion of the Raney alloy particles at least partially into the thermoplastic organic polymer material support particles, so that the resulting supported catalyst comprises 2 wt. % to 95 wt. % of the Raney alloy and 5 wt. % to 98 wt. % of the organic polymer material support, based on the total weight of the supported catalyst; and
   (4) cooling, then sieving, to obtain the particulate supported catalyst.

2. The process of claim 1, wherein the Raney alloy comprises at least one Raney metal and at least one leachable element.

3. The process of claim 2, wherein the at least one Raney metal is chosen from nickel, cobalt, copper, and iron, and the at least one leachable element is chosen from aluminum, zinc, and silicon.

4. The process of claim 2, wherein the weight ratio of the Raney metal to the leachable element in the Raney alloy is from 1:99 to 10:1.

5. The process of claim 4, wherein the weight ratio of the Raney metal to the leachable element in the Raney alloy is from 1:10 to 4:1.

6. The process of claim 1, wherein the organic polymer material is chosen from polypropylenes, Nylon-6, Nylon-66, polystyrenes, phenolic resins, epoxy resins, and mixtures and blends thereof.

* * * * *